United States Patent [19]

Jacobsen

[11] Patent Number: Plant 6,605

[45] Date of Patent: Feb. 14, 1989

[54] GERANIUM PLANT NAMED RED SILVER CROWN

[76] Inventor: Peter Jacobsen, P.O. Box 2, Hyde Park, Ontario, Canada

[21] Appl. No.: 89,520

[22] Filed: Aug. 26, 1987

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A geranium plant named Red Silver Crown, characterized by its bright red fading to red-pink flower color, variegated green and white leaves, short leaf internodes, good branching, and compact growth habit.

1 Drawing Sheet

The present invention comprises a new and distinct cultivar of geranium named Red Silver Crown. The new geranium is of the species *Pelargonium peltatum,* commonly referred to as an ivy geranium characterized by its trailing growth habit and generally ivy-shaped leaves.

Red Silver Crown is a sport discovered by applicant in a controlled environment in Hyde Park, Ontario, Canada in April 1984. The parent cultivar was a trailing ivy geranium which had red flowers, green non-variegated leaves, and long internodes. The precise identification and name of the parent cultivar are not known at this time. Red Silver Crown was discovered as one flowering plant within a bed of parent plants.

The first act of asexual reproduction of Red Silver Crown was accomplished when vegetative cuttings were taken in June 1984 in a controlled environment in Hyde Park, Ontario, Canada by a technician working under formulations established and supervised by Peter Jacobsen. Horticultural examination of selected units initiated in December, 1984 has demonstrated that the combination of characteristics as herein disclosed for Red Silver Crown are firmly fixed and are retained through successive generations of asexual reproduction. Red Silver Crown has not been observed under all possible environmental conditions. The phenotype may vary significantly with variations in environment such as temperature, light intensity, and day length. The following observations, measurements, and comparisons describe plants grown in Hyde Park, Ontario, Canada under conditions which approximate those generally used in commercial practice.

The following traits have been repeatedly observed and are determined to be basic characteristics of Red Silver Crown which in combination distinguish this geranium as a new and distinct cultivar.

1. Variegated leaf which consists of a white margin, a medium green center, and a light green zone intermediate the center and the margin.
2. Short leaf internodes.
3. Red flower color.
4. Compact growth habit.
5. Fast rooting.
6. No growth treatment is necessary for quality plant production.
7. Good branching.

Of the many commercial cultivars known to the present inventor, the most similar in comparison to Red Silver Crown are Red-Mini-Cascade and Red (Rose) Cascade. Reference is made to attached Chart A which compares certain characteristics of Red Silver Crown to those same characteristics of Red-Mini-Cascade and Red (Rose) Cascade. The measurements and comparative information appearing on Chart A was based on twelve (12) separate plants of each of the compared cultivars, with the numbers appearing being the average of the twelve measurements. Generally, in comparison to Red-Mini-Cascade, Red Silver Crown has variegated leaves, less branching, and shorter peduncle and pedicel lengths. In comparison to Red (Rose) Cascade, Red Silver Crown has variegated leaves, substantially shorter internodes, and shorter peduncle and pedicel lengths, and a somewhat smaller diameter umbel. The flower color of all three cultivars is approximately the same.

The accompanying photographic drawing shows typical flower and foliage characteristics of Red Silver Crown. The photograph is in black and white, with flowers and leaves being colored to depict true flower and leaf color.

In the following description color references are made to The Royal Horticultural Society Colour Chart. The color values were determined between 2:20 and 2:40 p.m. on June 15, 1987 under fluorescent light at Parrish, Fla.

Classification:

*Botanical.*—*Pelargonium peltatum.*

*Commercial.*—Ivy geranium, cv. Red Silver Crown.

INFLORESCENCE

A. Umbel:

*Average diameter.*—67 mm.

*Average depth.*—52 mm.

*Peduncle length.*—109 mm.

*Pedicel length.*—31 mm.

B. Corolla:

*Average diameter.*—37 mm.

*Form.*—5 petal single; nearly round.

*Color.*—Upper surface: 45B fading to 52A; photograph shows both fresh and faded colors. Fading begins on top two flower petals. Under surface: slightly lighter than values noted above.

C. Bud: Elongated and elliptic in shape.

D. Reproductive organs:

*Androecium.*—5–7 stamens.

*Gynoecium.*—5 lobes on stigma, color red; style light pink in color.

E. Spring flowering response period: In Hyde Park, Canada, nearly 100% of plants flowered within 13 weeks after planting unrooted cuttings.

F. Outdoor flower production: The flower count in Hyde Park, Canada in 1986 was an average of 25 flowers per plant (range was 16–39) for June through September. The wet summer was not ideal for flower production.

PLANT

A. Foliage:

*Form.*—5 lobed.

*Margin.*—Serrated.

*Color (zonation).*—The leaf has a white margin, followed by a light green zone (approximately 147C) which is variable in width. The center of the leaf is a medium green (approximately 147A-B).

*Tolerance of botrytis: Good.*

B. General appearance and form:

*Internode length.*—18 mm.

*Branching pattern.*—Good; an average of 2.83 branches per plant.

*Height.*—173 mm.

CHART A

| | RED SILVER CROWN | RED MINI CASCADE | RED CASCADE |
|---|---|---|---|
| Corolla Color | 46C top 51A bottom | 46C top 51A bottom | 46C top 51A bottom |
| Spring flowering response | 100% | 100% | 100% |
| Branching | 2.83 | 5.42 | 2.75 |
| Internode length | 18.42 mm | 18.67 mm | 35.83 mm |
| Leaf variegation | Yes | No | No |
| Umbel average diameter | 66.83 mm | 67.50 mm | 73.00 mm |
| Umbel average depth | 51.83 mm | 53.58 mm | 55.50 mm |
| Peduncle length | 109.25 mm | 124.00 mm | 132.83 mm |
| Pedicel length | 30.75 mm | 34.67 mm | 33.92 mm |
| Corolla average diameter | 37.42 mm | 39.50 mm | 41.50 mm |

I claim:

1. A new and distinct geranium plant named Red Silver Crown, as described and illustrated, and particularly characterized by its bright red facing to red-pink flower color, variegated green and white foliage, short leaf internodes, good branching, and compact growth habit.

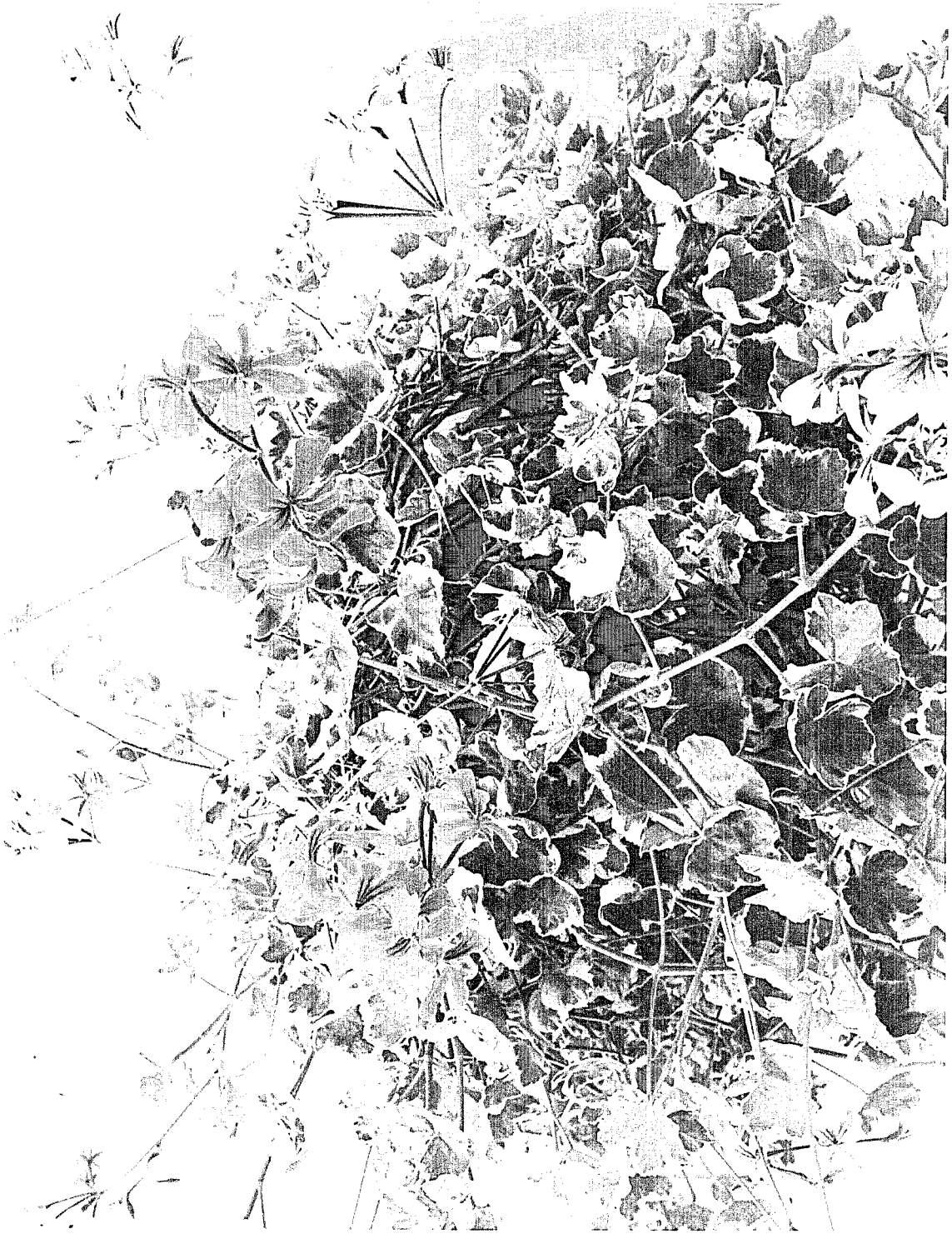

* * * * *